(12) United States Patent
Shomura et al.

(10) Patent No.: US 9,878,062 B2
(45) Date of Patent: Jan. 30, 2018

(54) ASEPTIC MANIPULATION SYSTEM

(71) Applicant: SHIBUYA CORPORATION, Ishikawa (JP)

(72) Inventors: Masaharu Shomura, Ishikawa (JP); Takuya Funazuka, Ishikawa (JP)

(73) Assignee: SHIBUYA CORPORATION, Ishikawa (JP)

( * ) Notice: Subject to any disclaimer, the term of this patent is extended or adjusted under 35 U.S.C. 154(b) by 0 days.

(21) Appl. No.: 15/112,248

(22) PCT Filed: Jan. 7, 2015

(86) PCT No.: PCT/JP2015/050262
§ 371 (c)(1),
(2) Date: Jul. 18, 2016

(87) PCT Pub. No.: WO2015/111431
PCT Pub. Date: Jul. 30, 2015

(65) Prior Publication Data
US 2016/0339130 A1      Nov. 24, 2016

(30) Foreign Application Priority Data
Jan. 27, 2014  (JP) .................................. 2014-012663

(51) Int. Cl.
*A61L 9/00* (2006.01)
*B01D 39/00* (2006.01)
(Continued)

(52) U.S. Cl.
CPC ............... *A61L 2/20* (2013.01); *C12M 37/00* (2013.01); *C12M 41/40* (2013.01); *F24F 3/161* (2013.01);
(Continued)

(58) Field of Classification Search
CPC ............... A61L 9/00; A61L 9/015; A61L 9/03
(Continued)

(56) References Cited

U.S. PATENT DOCUMENTS 5,356,335 A     10/1994  Matsui et al.
2006/0185189 A1   8/2006  Kawasaki
(Continued)

FOREIGN PATENT DOCUMENTS

EP   2363255   9/2011
GB   2257547   1/1993
(Continued)

OTHER PUBLICATIONS

Japanese Patent Office English Translation of JP 2012-29859.*
(Continued)

*Primary Examiner* — Monzer R Chorbaji
(74) *Attorney, Agent, or Firm* — Greenblum & Bernstein, P.L.C.

(57) ABSTRACT

A decontamination operation chamber is partitioned into a first operation chamber and a second operation chamber. A connecting portion that connects the first operation chamber and the second operation chamber can be closed. The pressure of the first operation chamber and the second operation chamber is adjusted by a pressure-adjusting mechanism. When the connecting portion is opened and the first operation chamber and the second operation chamber are connected, an inlet portion for the first operation chamber and an outlet portion for the second operation chamber are closed and air flow is generated from the second operation chamber to the first operation chamber by the pressure-adjusting mechanism. When carrying an object into an aseptic manipulation chamber, the object is housed in the first operation chamber and a first decontamination operation is performed, then the object is transferred to the second (Continued)

51, 52  AIR SUPPLY FAN (PRESSURE-ADJUSTING MECHANISM)
53, 54  AIR DISCHARGE FAN (PRESSURE-ADJUSTING MECHANISM)
85, 88, 95, 98  AIR VOLUME REGULATING VALVE (PRESSURE-ADJUSTING MECHANISM)

operation chamber and a second decontamination operation is performed.

8 Claims, 3 Drawing Sheets

(51) Int. Cl.
| | | |
|---|---|---|
| *F24F 7/007* | (2006.01) | |
| *A61L 2/20* | (2006.01) | |
| *F24F 3/16* | (2006.01) | |
| *C12M 1/12* | (2006.01) | |
| *C12M 1/34* | (2006.01) | |

(52) U.S. Cl.
CPC .................. *F24F 2003/1614* (2013.01); *F24F 2003/1628* (2013.01)

(58) Field of Classification Search
USPC ........... 422/305; 96/223, 226; 454/228, 237, 454/254
See application file for complete search history.

(56) References Cited

U.S. PATENT DOCUMENTS

| | | |
|---|---|---|
| 2011/0212513 A1 | 9/2011 | Yokoi et al. |
| 2013/0336844 A1 | 12/2013 | Yokoi et al. |
| 2016/0184814 A1 | 6/2016 | Funazuka et al. |

FOREIGN PATENT DOCUMENTS

| | | | | |
|---|---|---|---|---|
| JP | 03-039081 | | 2/1991 | |
| JP | 2005-143726 | | 6/2005 | |
| JP | 2009-125517 | | 6/2009 | |
| JP | 2010-51351 | | 3/2010 | |
| JP | 2012-29859 | * | 2/2012 | ............... A61L 2/20 |

OTHER PUBLICATIONS

Search Report issued by PCT patent office in PCT Patent Application No. PCT/JP2015/050262, dated Feb. 10, 2015.
Office Action issued in Japan Counterpart Patent Appl. No. 2014-012663, dated Oct. 3, 2017.

* cited by examiner

30 DECONTAMINATION CHAMBER 51, 52 AIR SUPPLY FAN (PRESSURE-ADJUSTING MECHANISM)
53, 54 AIR DISCHARGE FAN (PRESSURE-ADJUSTING MECHANISM)
85, 88, 95, 98 AIR VOLUME REGULATING VALVE (PRESSURE-ADJUSTING MECHANISM)

ASEPTIC MANIPULATION SYSTEM

TECHNICAL FIELD

The present invention relates to an aseptic manipulation system for performing an operation such as a cultivation of human cells, for example, in an aseptic manipulation chamber separated from the external air to keep it in an aseptic condition.

BACKGROUND ART

Conventionally, as disclosed in PATENT DOCUMENT 1, for example, an aseptic manipulation system is partitioned into an aseptic manipulation chamber, the inside of which is kept in an aseptic condition, and a pass box connected to the aseptic manipulation chamber. A communication portion formed between the aseptic manipulation chamber and the pass box, and an inlet portion provided in an outer wall of the pass box, can be hermetically closed by an open-close member, respectively. Microbes adhering to a surface of an object carried into the aseptic manipulation chamber are removed therefrom by decontamination gas (i.e., decontamination vapor) in the pass box. After that, the inside of the pass box is subjected to aeration, so that decontaminants remaining on the object and an inner wall of the pass box are removed, and the pass box and the aseptic manipulation chamber are then in communication with each other, and the object is transferred into the aseptic manipulation chamber.

According to the above-described conventional aseptic manipulation system, the inside of the pass box is filled with decontamination gas to remove microbes, so that not only the object but also the inner walls of the pass box, which has been opened to the external environment for introducing the object, are sterilized, and the pass box is then in communication with the aseptic manipulation chamber while keeping the sterilized condition. Therefore, the aseptic manipulation chamber and the pass box are maintained in a grade D cleanliness environment of air, which is a slightly higher cleanliness grade than the general environment.
PATENT DOCUMENT 1: Japanese Unexamined Patent Publication No. 2010-51351

SUMMARY OF THE INVENTION

Problems to be Solved by the Invention

The aeration of the pass box needs to be performed until the removal of the decontamination vapor from both the object and the inner wall is completed, and as the concentration of decontamination vapor becomes low, the rate of reduction of the concentration slows. Thus, there is a problem, in which the time for the decontamination will take too long. Further, when the carried object is a cultivation container, in which cells and the like are housed, an adverse effect can occur in which the object is exposed in an improper temperature condition for a long time, due to the supply of the decontamination vapor and the aeration. Furthermore, since such a cultivation container is not sufficiently airtight, there is a concern that a vaporized decontamination medium will flow into the container and affect the inside thereof.

The object of the present invention is to shorten the time required for the decontamination of the object carried into the aseptic manipulation chamber, and to be able to select the decontamination medium and the decontamination method in accordance with the carried object.

Means for Solving the Problems

An aseptic manipulation system of the present invention comprises an aseptic manipulation chamber, the inside of which is kept in an aseptic condition, and a decontamination chamber provided for removing microbes adhering to an object carried into the aseptic manipulation chamber from the outside thereof. The decontamination chamber has a first operation chamber provided with an inlet portion that can be closed, a second operation chamber connected to the first operation chamber and provided with an outlet portion that can be closed, and a closable communication portion for communicating between the first operation chamber and the second operation chamber, and is connected to a pressure-adjusting mechanism for adjusting the pressure of the first operation chamber and the second operation chamber. When the communication portion is open to communicate between the first operation chamber and the second operation chamber, the inlet portion and the outlet portion are closed, and an air current from the second operation chamber to the first operation chamber is generated by the pressure-adjusting mechanism. When an object is carried into the aseptic manipulation chamber from the outside thereof, the object is stored in the first operation chamber to undergo a first decontamination, the object is then moved from the first operation chamber to the second operation chamber through the communication portion to perform a second decontamination in the second operation chamber, after which the object is carried into the aseptic manipulation chamber.

The pressure-adjusting mechanism may comprise a first air supply and exhaust mechanism that supplies air to and exhausts air from the first operation chamber, and a second air supply and exhaust mechanism that supplies air to and exhausts air from the second operation chamber. In this case, the first and second air supply and exhaust mechanisms set the air supply amount to the second operation chamber greater than that to the first operation chamber, and set the air exhaust amount from the first operation chamber greater than that from the second operation chamber, in a state in which the communication portion is open.

As one embodiment, in the first decontamination performed in the first operation chamber, the first operation chamber can be filled with decontamination gas to apply the decontamination gas to an object that is to be carried into the aseptic manipulation chamber, and in the second decontamination performed in the second operation chamber, the decontamination gas residue remaining on the object can be removed. As another embodiment, in the first decontamination performed in the first operation chamber, microbes adhering to the object that is to be carried into the aseptic manipulation chamber can be removed using a first decontamination medium, and in the second decontamination performed in the second operation chamber, the microbes adhering to the object can be removed using a second decontamination medium different from the first decontamination medium.

Effects of the Invention

According to the present invention, the time required for the decontamination of the object carried into the aseptic manipulation chamber can be reduced, and the decontamination medium and the decontamination method in accordance with the carried object can be selected.

Figure 1:
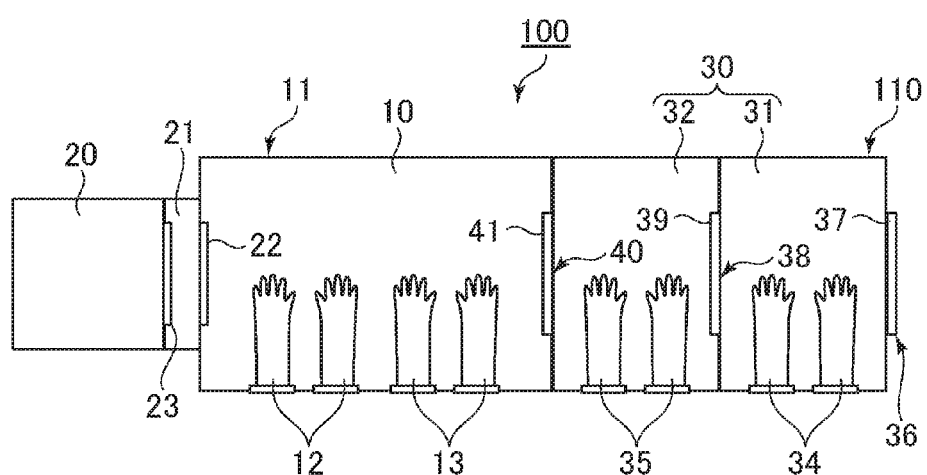
FIG. 1 A layout drawing showing components of an aseptic manipulation system to which a first embodiment of the present invention is applied.

EXPLANATION OF REFERENCES 10 aseptic manipulation chamber
30 decontamination chamber
31 first operation chamber
32 second operation chamber
36 inlet portion
38 communication portion
40 outlet portion
51, 52 air supply fan (pressure-adjusting mechanism)
53, 54 air discharge fan (pressure-adjusting mechanism)
85, 88, 95, 98 air volume regulating valve (pressure-adjusting mechanism)
A object

EMBODIMENT OF THE INVENTION

In the following, an aseptic manipulation system 100, which is an embodiment of the present invention, will be described with a first embodiment which is illustrated in the drawings. FIG. 1 shows a general structure of the aseptic manipulation system 100. The aseptic manipulation system includes an isolator 11 with an aseptic manipulation chamber 10 formed therein, and an inlet portion of the aseptic manipulation chamber 10 is connected to a pass box 110, where the inside of a decontamination chamber 30 for removing microbes adhering to an object carried into the aseptic manipulation chamber 10 from the outside of the aseptic manipulation system is formed. The decontamination chamber 30 is partitioned into a first operation chamber 31 and a second operation chamber 32. An incubator 20 for cultivating human cells, which have been treated in the aseptic manipulation chamber 10, can be attached to or detached from the aseptic manipulation chamber 10 on the side opposite to the decontamination chamber 30. Note that the first operation chamber 31 and the second operation chamber 32 may be defined by dividing the inside of the single pass box 110, or may be formed by connecting two independent pass boxes 110.

Gloves 12 and 13 are provided on a wall of the aseptic manipulation chamber 10 in order to perform various kinds of treatments on an object placed in the aseptic manipulation chamber 10 from a clean booth (not shown) provided outside of the aseptic manipulation chamber 10. Similarly, gloves 34 and 35 are provided in the first operation chamber 31 and the second operation chamber 32 of the decontamination chamber 30.

The first operation chamber 31 is located on an opposite side of the aseptic manipulation chamber 10 with respect to the second operation chamber 32, and an inlet portion 36 of the first operation chamber 31 can be closed by a first closing member 37. The second operation chamber 32 is connected to the first operation chamber 31, and a communication portion 38 communicating between the first operation chamber 31 and the second operation chamber 32 can be closed by a second closing member 39. An outlet portion 40 of the second operation chamber 32, or a connecting portion to the aseptic manipulation chamber 10 can be closed by a third closing member 41.

The aseptic manipulation chamber 10, the first operation chamber 31, and the second operation chamber 32 are constructed such that the inside pressure of each of the chambers is adjusted by a pressure-adjusting mechanism described later, and the pressure relationships among each of the chambers are controlled in such a manner that the air pressure in the first operation chamber 31 is higher than the ambient pressure, the air pressure in the second operation chamber 32 is lower than that of the first operation chamber 31, the air pressure in the aseptic manipulation chamber 10 is higher than that of the first operation chamber 31, and all of the pressure is positive in comparison with the ambient pressure. Thus, the air pressure in the second operation chamber 32 provided between the other chambers is kept lower than the aseptic manipulation chamber 10 and the first operation chamber 31 so that air is prevented from flowing between the aseptic manipulation chamber 10 and the first operation chamber 31. Due to this, even if the aseptic manipulation chamber 10 and the first operation chamber 31 are communicating with each other, the ambient air contaminated by the ambient environment is prevented from flowing into the aseptic manipulation chamber 10, and pathogens such as viruses are prevented from flowing out from the aseptic manipulation chamber 10 to the ambient environment.

When the incubator 20 is attached to the aseptic manipulation system 100, the incubator 20 is connected to the aseptic manipulation chamber 10 through a connecting portion 21. A partition wall between the aseptic manipulation chamber 10 and the connecting portion 21 is opened and closed by a first open-close member 22, and a portion between the connecting portion 21 and the incubator 20 is opened and closed by a second open-close member 23 provided in the incubator 20.

Figure 2:
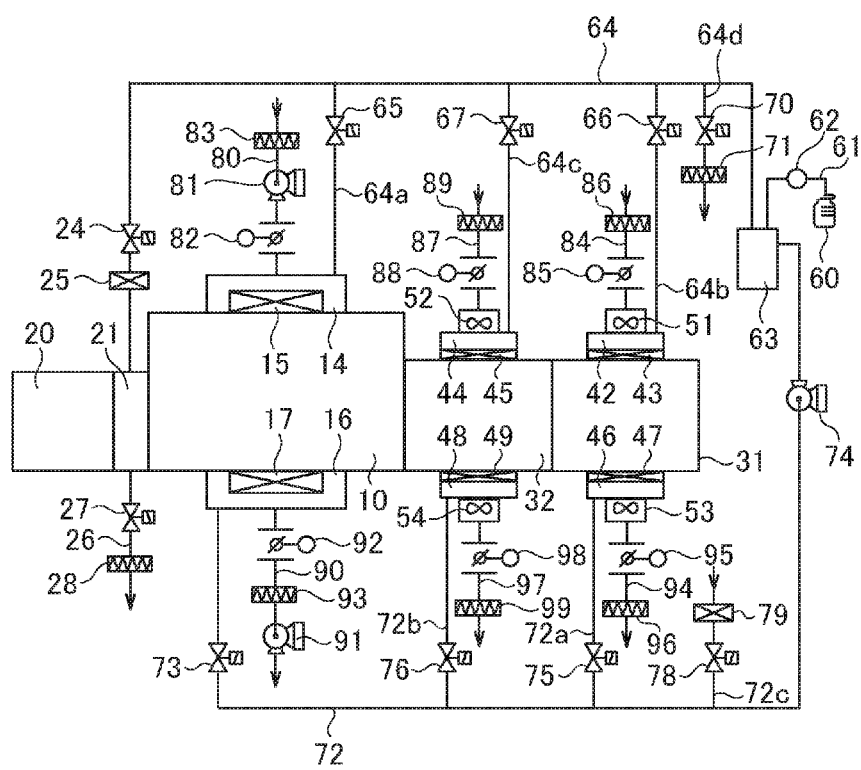
FIG. 2 A diagram showing a fluid supply circuit for supplying and discharging decontamination gas and clean air in the aseptic manipulation system shown in FIG. 1.

With reference to FIG. 2, the construction of a decontamination gas supply circuit, which supplies decontamination gas (decontamination vapor) and clean gas to the aseptic manipulation chamber 10, the decontamination chamber 30, and the connecting portion 21, will be described below. In this embodiment, the decontamination gas is hydrogen peroxide vapor, and a hydrogen peroxide aqueous solution is stored in a bottle 60. The hydrogen peroxide aqueous solution is supplied from the bottle 60 to an evaporator 63 in a predetermined quantity by a pump 62, which is provided in a decontamination medium supply passage 61, and is heated by the evaporator 63 to form hydrogen peroxide vapor. A circulation passage 72 is connected to an inlet of the evaporator 63, and hydrogen peroxide that is generated is discharged from the evaporator 63 by an operation of a circulation blower 74 provided in the circulation passage 72. A decontamination gas supply passage 64 connected to an outlet of the evaporator 63 is connected to the aseptic manipulation chamber 10, the first operation chamber 31, and the second operation chamber 32 through open-close valves 65, 66, and 67.

A gas supply chamber 14 is provided on a top side of the aseptic manipulation chamber 10, and a first branch passage 64a of the decontamination gas supply passage 64 is connected to the gas supply chamber 14. A HEPA filter 15 is arranged in the gas supply chamber 14, and hydrogen peroxide vapor supplied to the gas supply chamber 14 enters the aseptic manipulation chamber 10 through the HEPA filter 15.

Similarly, a gas supply chamber 42 is provided on a top side of the first operation chamber 31, and a second branch passage 64b of the decontamination gas supply passage 64 is connected to the gas supply chamber 42. A HEPA filter 43 is arranged in the gas supply chamber 42, and hydrogen peroxide vapor supplied to the gas supply chamber 42 enters the first operation chamber 31 through the HEPA filter 43. Regarding the second operation chamber 32 as well, hydrogen peroxide vapor is supplied from a third branch passage 64c of the decontamination gas supply passage 64 to a gas supply chamber 44, and enters the second operation chamber 32 through a HEPA filter 45.

The connecting portion 21 is connected to the decontamination gas supply passage 64 through an open-close valve 24 and a HEPA filter 25. Namely, hydrogen peroxide vapor passing through the decontamination gas supply passage 64 is supplied to the inside of the connecting portion 21 through the HEPA filter 25.

In a fourth branch passage 64d of the decontamination gas supply passage 64, a pressure-adjusting valve 70 is provided downstream of the circulation blower 74 so that when the circulation blower 74 is operated, gas is discharged from the decontamination gas supply passage 64 to reduce the amount of gas impelled by the circulation blower 74, and the pressure is adjusted lower in the aseptic manipulation chamber 10, the first operation chamber 31, and the second operation chamber 32. Note that a catalyst 71 is arranged in an open end of the fourth branch passage 64d to prevent the outflow of a toxic substance outside of the aseptic manipulation system 100.

A gas discharge chamber 16 is provided on a bottom side of the aseptic manipulation chamber 10, and a HEPA filter 17 is arranged in the gas discharge chamber 16. The gas discharge chamber 16 is connected to the circulation passage 72, which is connected to the inlet of the evaporator 63, and the circulation passage 72 is provided with an open-close valve 73. Therefore, gas in the aseptic manipulation chamber 10 is discharged into the gas discharge chamber 16 through the HEPA filter 17 by a discharge operation of the circulation blower 74, and flows back to the evaporator 63 through the circulation passage 72.

Similarly, a HEPA filter 47 is arranged in a gas discharge chamber 46 formed on a bottom side of the first operation chamber 31, and a HEPA filter 49 is arranged in a gas discharge chamber 48 formed on a bottom side of the second operation chamber 32. The gas discharge chambers 46 and 48 are connected to first and second branch passages 72a and 72b of the circulation passage 72, in which open-close valves 75 and 76 are provided. Thereby, gas in the first operation chamber 31 and the second operation chamber 32 is discharged into the gas discharge chambers 46 and 48 through the HEPA filters 47 and 49, and flows back to the evaporator 63 through the circulation passage 72.

In a third branch passage 72c of the circulation passage 72, a pressure-adjusting valve 78 is provided upstream of the circulation blower 74 so that when the circulation blower 74 is operated, ambient air flows into the circulation passage 72 to increase the amount of gas impelled by the circulation blower 74, and the pressure is adjusted higher in the aseptic manipulation chamber 10, the first operation chamber 31, and the second operation chamber 32. An open end of the third branch passage 72c is open to the outside of the aseptic manipulation system through the HEPA filter 79.

A structure for supplying clean gas into the aseptic manipulation chamber 10, the first operation chamber 31 and the second operation chamber 32 is described below. A first gas supply passage 80 is connected to the gas supply chamber 14 of the aseptic manipulation chamber 10. An air supply blower 81 is provided in the first gas supply passage 80, and an air volume regulating valve 82 is provided between the air supply blower 81 and the gas supply chamber 14. A catalyst 83 is provided in an open end of the first air supply passage 80.

According to the construction described above, by opening the air volume regulating valve 82 and operating the air supply blower 81, air flows into the gas supply chamber 14 from the outside through the first gas supply passage 80 and is purified by the HEPA filter 15 before entering the aseptic manipulation chamber 10. Further, by adjusting the opening degree of the air volume regulating valve 82 or the air flow volume of the air supply blower 81, the volume of air supplied to the aseptic manipulation chamber 10 can be increased or decreased.

An air supply fan 51 is provided for the gas supply chamber 42 of the first operation chamber 31, and a second gas supply passage 84 is connected to the air supply fan 51. An air volume regulating valve 85 is provided in the second gas supply passage 84, and a catalyst 86 is provided in an open end of the second gas supply passage 84. Similarly, an air supply fan 52 is provided for the gas supply chamber 44 of the second operation chamber 32, and a third gas supply passage 87 is connected to the air supply fan 52. An air volume regulating valve 88 is provided in the third gas supply passage 87, and a catalyst 89 is provided in an open end of the third gas supply passage 87.

According to the construction described above, by opening the air volume regulating valve 85 and operating the air supply fan 51, air flows into the gas supply chamber 42 from the outside through the second gas supply passage 84 and is purified by the HEPA filter 43 before entering the first operation chamber 31. Further, by adjusting the opening degree of the air volume regulating valve 85 or the air flow volume of the air supply fan 51, the volume of air supplied to the first operation chamber 31 can be increased or decreased. Similarly, by opening the air volume regulating valve 88 and operating the air supply fan 52, air flows into the gas supply chamber 44 from the outside through the third gas supply passage 87 and is purified by the HEPA filter 45 before entering the second operation chamber 32. Further, by adjusting the opening degree of the air volume regulating valve 88 or the air flow volume of the air supply fan 52, the volume of air supplied to the second operation chamber 32 can be increased or decreased.

A structure for discharging gas from the aseptic manipulation chamber 10, the first operation chamber 31, the second operation chamber 32, and the connecting portion 21 is described below. A first gas discharge passage 90 is connected to the gas discharge chamber 16 of the aseptic manipulation chamber 10, and an air discharge blower 91 is provided in the first gas discharge passage 90. An air volume regulating valve 92 and a catalyst 93 are provided between the air discharge blower 91 and the gas discharge chamber 16.

According to the construction described above, by opening the air volume regulating valve 92 and operating the air discharge blower 91, air passing through the HEPA filter 17 and the air discharge chamber 16 from the aseptic manipulation chamber 10 is discharged outside through the first gas discharge passage 90. Further, by adjusting the opening degree of the air volume regulating valve 92 or the air flow volume of the air discharge blower 91, the volume of air discharged from the aseptic manipulation chamber 10 can be increased or decreased. The air volume regulating valve 92, which increases or decreases the discharged air volume, the air discharge blower 91, the air volume regulating valve 82, which increases or decreases the supplied air volume, and the air supply blower 81 form an air supply and exhaust mechanism for the aseptic manipulation chamber 10.

An air discharge fan 53 is provided for the gas discharge chamber 46 of the first operation chamber 31, and a second gas discharge passage 94 is connected to the air discharge fan 53. An air volume regulating valve 95 and a catalyst 96 are provided in the second gas discharge passage 94. Similarly, an air discharge fan 54 is provided for the gas discharge chamber 48 of the second operation chamber 32, and a third gas discharge passage 97 is connected to the air discharge fan 54. An air volume regulating valve 98 and a catalyst 99 are provided in the third gas discharge passage 97.

According to the construction described above, by opening the air volume regulating valve 95 and operating the air discharge fan 53, air passing through the HEPA filter 47 and the air discharge chamber 46 from the first operation chamber 31 is discharged outside through the second gas discharge passage 94. Further, by adjusting the opening degree of the air volume regulating valve 95 or the air flow volume of the air discharge fan 53, the volume of air discharged from the first operation chamber 31 can be increased or decreased. The air volume regulating valve 95, which increases or decreases the discharged air volume, the air discharge fan 53, the air volume regulating valve 85, which increases or decreases the supplied air volume, and the air supply fan 51 form a first air supply and exhaust mechanism for the first operation chamber 31. Similarly, by opening the air volume regulating valve 98 and operating the air discharge fan 54, air passing through the HEPA filter 49 and the air discharge chamber 48 from the second operation chamber 32 is discharged outside through the third gas discharge passage 97. Further, by adjusting the opening degree of the air volume regulating valve 98 or the air flow volume of the air discharge fan 54, the volume of air discharged from the second operation chamber 32 can be increased or decreased. The air volume regulating valve 98, which increases or decreases the discharged air volume, the air discharge fan 54, the air volume regulating valve 88, which increases or decreases the supplied air volume, and the air supply fan 52 form a second air supply and exhaust mechanism for the second operation chamber 32.

Further, the air supply and exhaust mechanism for the aseptic manipulation chamber 10, the first air supply and exhaust mechanism for the first operation chamber 31, and the second air supply and exhaust mechanism for the second operation chamber 32 can adjust the pressure in each of the aseptic manipulation chamber 10, the first operation chamber 31, and the second operation chamber 32 by increasing and decreasing the supplied air volume and the discharged air volume of the mechanisms, and the pressure-adjusting mechanism of the present aseptic manipulation system 100 is formed by combining all the air supply and exhaust mechanisms connected to each other. The operations of these air supply and exhaust mechanisms are controlled in association with each other by a control unit not shown. Due to this, the pressure in each of the chambers can be maintained within a predetermined range, and the pressure relationship among the chambers can be maintained at a predetermined condition.

A gas discharge passage 26 is connected to the connecting portion 21 on the side opposite to the decontamination gas supply passage 64. An open-close valve 27 is provided in the gas discharge passage 26, and a catalyst 28 is arranged in an open end of the gas discharge passage 26.

Figure 3:
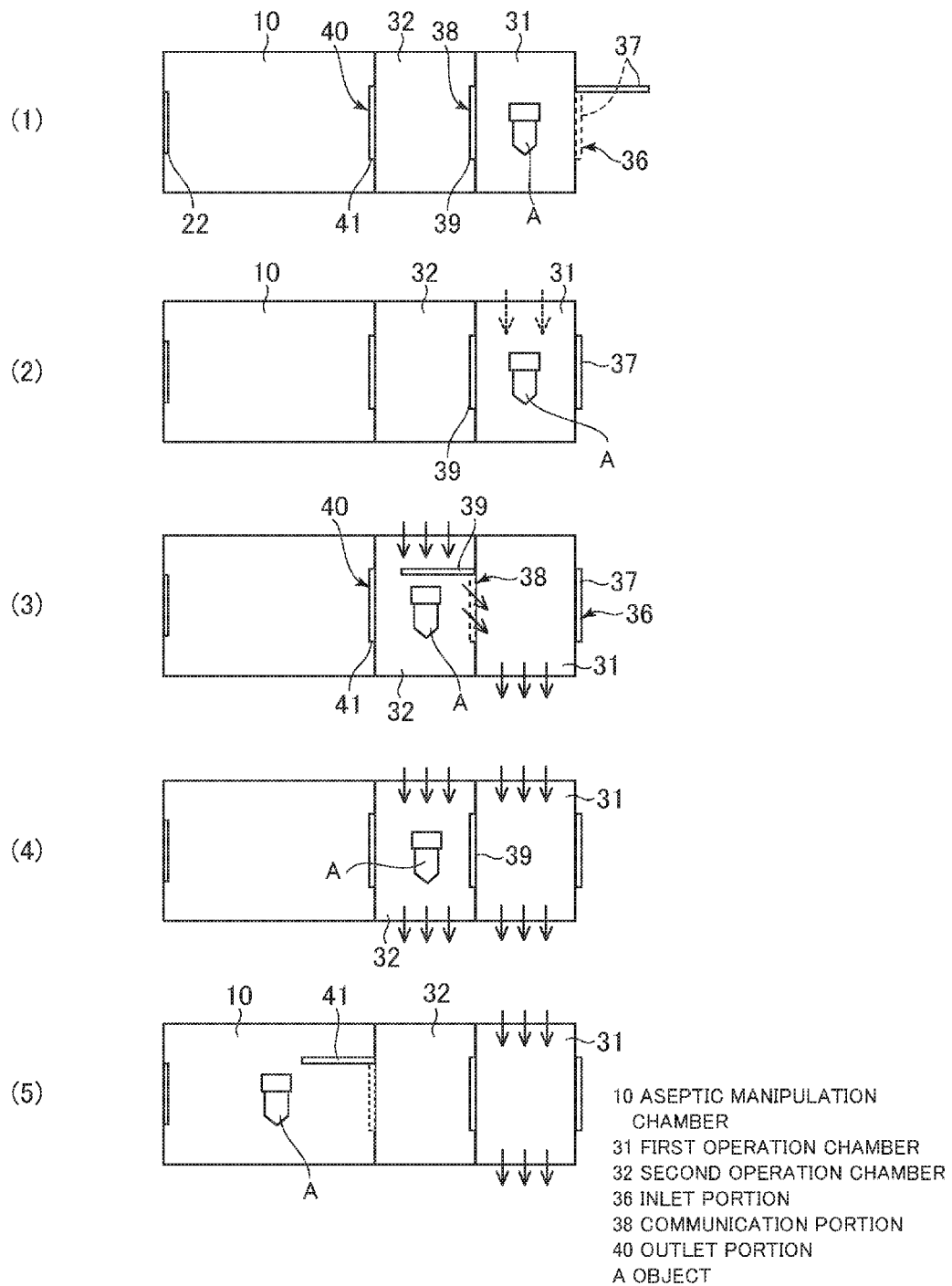
FIG. 3 A diagram showing the operations of the aseptic manipulation system to which the first embodiment is applied.

With reference to FIGS. 2 and 3, an operation of the embodiment will be described. Note that the incubator 20 and the connecting portion 21 are omitted from FIG. 3.

Before starting the operation, the inside of each of the aseptic manipulation chamber 10, the first operation chamber 31, and the second operation chamber 32 is supplied with hydrogen peroxide vapor, and aeration is carried out for the purpose of decontamination; and further, the air supply and discharge procedures are carried out by the air supply and exhaust mechanism for the aseptic manipulation chamber 10, the first air supply and exhaust mechanism for the first operation chamber 31, and the second air supply and exhaust mechanism for the second operation chamber 32, so that the inside of each of the chambers is maintained in an aseptic condition by keeping the inside pressure positive relative to the external environment using the pressure-adjusting mechanism, with the highest pressure maintained in the aseptic manipulation chamber 10 and the second highest pressure maintained in the first operation chamber 31.

When the first closing member 37 is opened, and an object A to be subjected to a treatment in the aseptic manipulation chamber 10 is placed in the first operation chamber 31, the communication portion 38 between the first operation chamber 31 and the second operation chamber 32 is closed by the second closing member 39, and the outlet portion 40 of the second operation chamber 32 is closed by the third closing member 41. When the object A is carried into the first operation chamber 31 through the inlet portion 36, the first closing member 37 is closed, and the first operation chamber 31 is hermetically isolated from the outside (Step (1)). In this state, although the first operation chamber 31 is in communication with the external environment by opening the first closing member 37, since the inside pressure of the first operation chamber 31 is maintained at a positive relative pressure by the pressure-adjusting mechanism, air from the external environment does not flow into the first operation chamber 31. The second closing member 39 is closed, so that the second closing member 39 does not communicate with the external environment.

In step (2), a first decontamination is performed on object A stored in the first operation chamber 31. That is, the open-close valves 66 and 75 are open and the circulation blower 74 is actuated so that hydrogen peroxide vapor generated in the evaporator 63 is supplied to the first operation chamber 31 through the second branch passage 64*b*, and flows back to the evaporator 63 through the first branch passage 72*a*. At the same time, the air volume regulating valves 85 and 95 are closed and the air supply fan 51 and the air discharge fan 53 are stopped so that the first operation chamber 31 is maintained at a positive relative pressure controlled by the open-close operations of the pressure-adjusting valves 70 and 78. The first operation chamber 31 is filled with hydrogen peroxide vapor, which acts on the object A to remove microbes adhering to a surface of the object A and also removes microbes adhering to the inner walls of the first operation chamber 31, which has been exposed to the external environment by opening the first closing member 37.

An initial aeration is carried out in the first operation chamber 31 when a predetermined amount of hydrogen peroxide vapor has been supplied to the operation chamber 31. At this time, although the operation of the pump 62, which supplies the hydrogen peroxide vapor, is stopped, the open-close valves 66 and 75 are open and the circulation blower 74 is actuated to ventilate the pipes. On the other hand, the air volume regulating valves 85 and 95 are opened by a predetermined degree and the air supply fan 51 and the air discharge fan 53 are actuated by a predetermined volume of air. Due to this, while air from the external environment of the aseptic manipulation system 100 flowing through the second gas supply passage 84 is purified by the HEPA filter 43 and supplied to the first operation chamber 31, in which the pressure condition is maintained, gas containing hydrogen peroxide in the first operation chamber 31 passes through the second gas discharge passage 94, toxic substances contained in the gas are removed by the catalyst 96, and the gas is discharged to the outside of the aseptic manipulation system 100. The initial aeration is continued until the residual hydrogen peroxide concentration in the chamber drops to a predetermined value. Note that the air supply volume and the air discharge volume at this time are adjusted to levels greater than those maintained for the pressure relationships among the chambers when a decontamination is not performed.

In step (3), the second closing member 39 is open, and the object A is transferred into the second operation chamber 32 from the first operation chamber 31 through the communication portion 38. The transfer of the object A is carried out while the communication portion 38 is open for communication between the first operation chamber 31 and the second operation chamber 32, and the inlet portion 36 and the outlet portion 40 are closed. Immediately before the transfer, in the second operation chamber 32 the air volume regulating valves 88 and 98 are opened by a predetermined opening degree, the air supply fan 52 and the air discharge fan 54 are operated at a predetermined air volume, and thus, the inside pressure of the second operation chamber 32 is maintained at a positive pressure lower than that of the first operation chamber 31, while the initial aeration is continuously performed in the first operation chamber 31. In this embodiment, with the opening operation of the second closing member 39, the air volume regulating valves 85 and 98 are closed, the air supply fan 51 and the air discharge fan 54 are stopped, and the air supply volume controlled by the air volume regulating valve 88 and the air supply fan 52 is adjusted by the pressure-adjusting mechanism to be greater than the air discharge volume controlled by the air volume regulating valve 95 and the air discharge fan 53.

Therefore, when the second closing member 39 is open, it generates a strong current of air that flows from an upper portion of the second operation chamber 32 to a lower portion of the first operation chamber 31, so that the atmosphere containing the decontaminants in the first operation chamber 31 is prevented from flowing into the second operation chamber 32. Due to this, air in the first operation chamber 31 is prevented from being drawn into the second operation chamber 32 with the opening operation of the second closing member 39, and thus, any decontaminants remaining in the first operation chamber 31 do not flow into the second operation chamber 32. During this operation, the positive pressure conditions of the first operation chamber 31 and the second operation chamber 32 relative to the external environment are maintained.

Thus, for generating the air current from the second operation chamber 32 to the first operation chamber 31, in this example, the air volume regulating valves 88 and 95 are open, the air volume regulating valves 85 and 98 are closed, the air supply fan 52 and the air discharge fan 53 are actuated, and the air supply fan 51 and the air discharge fan 54 are stopped. In another example, all of the air supply fans 51 and 52 and the air discharge fans 53 and 54 may be operated, and the air volume regulating valves 85 and 98 may be opened by a relatively small opening degree. That is to say, a control may be performed such that the air supply volume for the second operation chamber 32 is greater than that for the first operation chamber 31 while the air discharge volume for the first operation chamber 31 is greater than that for the second operation chamber 32, due to which the pressure in the second operation chamber 32 becomes higher than that in the first operation chamber 31 and a current flowing from the second operation chamber 32 to the first operation chamber 31 is generated. Note, in this case, the sum of the air supply volumes in the first operation chamber 31 and the second operation chamber 32 should be greater than the sum of the air discharge volumes, so that the pressure in all of these chambers is positive relative to the external environment.

After step (3), step (4) is performed, in which the second closing member 39 is closed, and a separate aeration for the object A is carried out as a second decontamination in the second operation chamber 32. At this time, regarding the first operation chamber 31, the air volume regulating valves 85 and 95 are open by a predetermined opening degree, and the air supply fan 51 and the air discharge fan 53 are actuated for a predetermined volume of air so that aeration for the inner wall surfaces continues from the initial aeration. Regarding the second operation chamber 32, the air volume regulating valves 88 and 98 are open by a predetermined opening degree, and the air supply fan 52 and the air discharge fan 54 are actuated for a predetermined volume of air. At this time, the air supply volume and the air discharge volume are controlled at levels greater than those for maintaining the pressure relationships with the aseptic manipulation chamber 10 and the first operation chamber 31, and thus, the ventilation efficiency is enhanced so that a large volume of fresh air makes contact with the object A in a short time to quickly remove the decontaminants from the object A. During this operation, the pressure in the first operation chamber 31 and the second operation chamber 32 is maintained positive relative to the external environment.

When the separate aeration for the second operation chamber 32 has been completed, step (5) is performed, in which the third closing member 41 is opened and the object A is carried into the aseptic manipulation chamber 10. At this time, regarding the first operation chamber 31, the open conditions of the air volume regulating valves 85 and 95 are maintained, and the air supply fan 51 and the air discharge fan 53 are continuously actuated, so that the aeration is continuously carried out. On the other hand, regarding the second operation chamber 32, the opening degrees of the air volume regulating valves 88 and 98 and the amounts of air flow generated by the air supply fan 52 and the air discharge fan 54 are adjusted so that the air supply volume and the air discharge volume are decreased to return to a control state, in which the usual pressure relationship is maintained.

After step (5), the third closing member 41 is closed, and the object A is used in the aseptic manipulation chamber 10.

When the first decontamination is performed in the first operation chamber 31, or when decontamination gas is supplied to the aseptic manipulation chamber 10, the first operation chamber 31, and the second operation chamber 32, in other words when the circulation blower 74 blows air, the pressure in the aseptic manipulation chamber 10, the first operation chamber 31, and the second operation chamber 32 is adjusted by an adjusting mechanism composed of the pressure-adjusting valves 70 and 78, in which operations are controlled by a control mechanism (not shown). That is, when the pressure becomes higher than a set value, the pressure-adjusting valve 70 is opened to discharge gas through the fourth branch passage 64d, and when the pressure becomes lower than a set value, the pressure-adjusting valve 78 is opened to allow ambient air into the third branch passage 72c so that the pressure in each of the chambers is maintained positive relative to the external environment.

When decontamination has been completed in the incubator 20 and it is going to be connected to the aseptic manipulation chamber 10, before communication between it and the aseptic manipulation chamber 10 decontamination gas is supplied to the interior of the connecting portion 21 to decontaminate the portion exposed to the external environment. That is, the front face of the incubator 20, to which the second open-close member 23 is provided, is initially in tight contact with the connecting portion 21 to form a hermetically closed inside space in the connecting portion 21. Next, in a state in which the first open-close member 22 of the aseptic manipulation chamber 10 and the second open-close member 23 of the incubator 20 are closed, the pressure-adjusting valve 78 is opened and the circulation blower 74 is actuated to send hydrogen peroxide vapor generated in the evaporator 63 to the decontamination gas supply passage 64, and the open-close valve 24 is opened to supply hydrogen peroxide vapor to the interior of the connecting portion 21. Due to this, microbes are removed from the entire interior of the connecting portion 21, which includes the exterior of the first open-close member 22 and its neighboring portion, and the exterior of the second open-close member 23 and its neighboring portion, which have been exposed to the external environment. After that, the open-close valve 27 is opened and the circulation blower 74 blows air while the supply of hydrogen peroxide vapor by the pump 62 to the evaporator 63 is stopped, to carry out aeration for a predetermined period of time. When these series of decontaminating operations are completed, the operator inserts his hands into the gloves 12 to open the first open-close member 22, then opens the second open-close member 23 with the gloves and carries an object such as a cultivation container into the incubator 20 from the aseptic manipulation chamber 10.

In the embodiment as described above, the decontamination chamber 30, which is provided for removing microbes adhering to the object A to be carried into the aseptic manipulation chamber 10, is partitioned into the first operation chamber 31 and the second operation chamber 32. After decontaminating object A with hydrogen peroxide vapor (decontamination gas) as the first decontamination in the first operation chamber 31, the object A is moved to the second operation chamber 32 to undergo the separate aeration as the second decontamination. The object A is the only target aerated in the second operation chamber 32, and in the first operation chamber 31 aeration is performed independently from the second operation chamber 32. That is, in the decontamination chamber 30, in which decontamination has been carried out, it is not necessary to aerate both the object and the decontamination chamber 30, and thus, the time required for the decontamination and the aeration of object A can be shortened.

Next, a second embodiment will be described below. As described above, the first embodiment is constructed such that decontamination gas composed of hydrogen peroxide vapor acts upon the object A in the first decontamination operation performed in the first operation chamber 31, and the separate aeration is performed in the second decontamination in the second operation chamber 32 to remove any decontamination gas residue remaining on the object A. Conversely, in the second embodiment, microbes adhering to the object A are removed using a first decontamination medium in the first decontamination operation performed in the first operation chamber 31, and microbes adhering to the object A are also removed using a second decontamination medium in the second decontamination operation performed in the second operation chamber 32.

That is, when the object A is a cultivation container storing cells, in the decontamination using decontamination gas that is gasified by heating, a harmful effect can occur when the cells are exposed to abrupt temperature variation, and when the cultivation container is not hermetically sealed, the decontamination gas may flow into the container, which may affect the cultivation of cells. Thus, in the second embodiment, a surface of the object is sprayed with liquid decontaminant, or wiped by a nonwoven fabric soaked in the liquid decontaminant. In this case, microbe removal is not also performed for the inside of the decontamination chamber 30 which has been exposed to the external environment, as in a case of the decontamination using the decontamination gas. Namely, in the embodiment, the decontamination chamber 30 is partitioned into the first operation chamber 31 and the second operation chamber 32, and the second operation chamber 32 is provided between the first operation chamber 31, which has been exposed to the external environment and stores the object, and the aseptic manipulation chamber 10. Furthermore, when the first operation chamber 31 and the second operation chamber 32 are in communication, an air current flowing from the second operation chamber 32 to the first operation chamber 31 is generated by a pressure-adjusting mechanism. Therefore, the first operation chamber 31, which has been exposed to the external environment, and the aseptic manipulation chamber 10 do not directly communicate with each other, and thus, the atmosphere of the first operation chamber 31 does not flow into the second operation chamber 32 or the aseptic manipulation chamber 10. Due to this, relative to an external environment of grade D, the first operation chamber 31, in which the cleanliness is kept higher than the external environment, is set to a grade C cleanliness, the second operation chamber 32 is set to a grade B cleanliness, and the aseptic manipulation chamber 10 is set to a grade A cleanliness.

For the decontamination medium used in the second embodiment, general antiseptic solutions or germicides such as alcohol (i.e., ethanol for disinfection), oxydol (i.e., hydrogen peroxide solution), peracetic acid, and sodium hypochlorite, which are liquid at normal temperature, can be used.

The second embodiment can be used together with the first embodiment, and can be used when the object is a cultivation container storing cells, for which a gas decontamination medium such as hydrogen peroxide vapor cannot be used as the decontamination medium, or which cannot be exposed to a high temperature during the decontamination. Specifically, in the aseptic manipulation system 100 identical to the first embodiment, the inside of each of the aseptic manipulation chamber 10, the first operation chamber 31, and the second operation chamber 32 is decontaminated and maintained at a positive pressure higher than the external environment to keep sterile, in which the pressure relationship among the chambers is maintained such that the pressure of the aseptic manipulation chamber 10 is the highest, and the pressure of the first operation chamber 31 is the second highest, and in this state, the first closing member 37 is opened to store an object A such as a cultivation container in the first operation chamber 31, similar to step (3) of FIG. 3. In step (2), the external operator inserts his hands into the gloves 34 to wipe the object A with a nonwoven fabric soaked in alcohol to remove microbes adhering to the object's surface. This is the first decontamination in the second embodiment.

In step (3), similarly to the first embodiment, the second closing member 39 is opened to move the object A to the second operation chamber 32, while the first closing member 37 and the third closing member 41 are closed. At this time, similarly to the first embodiment, by the operations of the supply and exhaust mechanism for each of the first operation chamber 31 and the second operation chamber 32, a strong current of air flows from an upper portion of the second operation chamber 32 to a lower portion of the first operation chamber 31 so that the atmosphere in the first operation chamber 31, which has been exposed to the external environment for carrying the object A, does not flow into the second operation chamber 32. In subsequent step (4), after the second closing member 39 is closed, the external operator inserts his hands into the gloves 35 to wipe the object A with a nonwoven fabric soaked in peracetic acid solution, to remove microbes adhering to the object's surface. This is the second decontamination in the second embodiment.

As described above, by varying the decontamination medium used in the first decontamination in the first operation chamber 31 from the medium used in the second decontamination in the second operation chamber 32, it becomes possible that various kinds of microbes, germs, and viruses, which have different tolerances, are comprehensively removed. After microbes and the like have been fully removed from the object A, the process goes to step (5), in which the third closing member 41 is opened, and the object A is carried into the aseptic manipulation chamber 10.

In the second embodiment described above, the inside of the decontamination chamber 30, which is exposed to the external environment when introducing the object into the chamber, is not decontaminated along with the decontamination of the object. However, the decontamination chamber 30 is partitioned into the first operation chamber 31 and the second operation chamber 32, and when the first operation chamber 31 and the second operation chamber 32 are in communication with each other, a current of air flows from the second operation chamber 32 to the first operation chamber 31 to prevent the movement of the atmosphere. Therefore, the atmosphere of the first operation chamber 31, which has been exposed to the external environment, does not flow into the second operation chamber 32, so that invasions of microbes, germs, and viruses into the aseptic manipulation chamber 10 can be avoided similarly to the first embodiment. Accordingly, in the aseptic manipulation system 100 disposed in a grade D cleanliness environment of air, it is possible to adopt a proper decontamination medium and method other than decontamination gas for the decontamination of an object to be transferred into the system. Further, after the decontamination in the first operation chamber 31, the use of a different decontamination medium in the second operation chamber 32 to carry out the other decontamination can produce an improved decontamination effect.

Note that the construction of the inventive aseptic manipulation system 100 corresponding to the first and second embodiments is not restricted to that composed of the aseptic manipulation chamber 10, the first operation chamber 31, and the second operation chamber 32, but instead can include an intermediate chamber such as an air lock chamber, which would avoid the need for direct communication if placed in front of the first operation chamber 31 or between the aseptic manipulation chamber 10 and the second operation chamber 32. Further, the pressure relationship among the chambers is not restricted to that in which the pressure of the second operation chamber 32 is kept lower than the first operation chamber 31. The first operation chamber 31 and the second operation chamber 32 may have the same air pressure if it is lower than the pressure of the aseptic manipulation chamber 10 and positive relative to the external environment, or the pressure of the second operation chamber 32 may be higher than that of the first operation chamber 31 as long as the pressure is lowered on a step-wise basis from the aseptic manipulation chamber 10.

The invention claimed is:

1. An aseptic manipulation system comprising an aseptic manipulation chamber, the inside of which is kept in an aseptic condition, and a decontamination chamber provided for removing microbes adhering to an object carried into the aseptic manipulation chamber from the outside thereof;
   the decontamination chamber having a first operation chamber provided with an inlet portion that can be closed, a second operation chamber connected to the first operation chamber and provided with an outlet portion that can be closed, and a closable communication portion for communicating between the first operation chamber and the second operation chamber, the decontamination chamber being connected to a pressure-adjusting mechanism that adjusts the pressure of the first operation chamber and the second operation chamber;
   when the communication portion is open for communication between the first operation chamber and the second operation chamber, the inlet portion and the outlet portion are closed, and an air current from the second operation chamber to the first operation chamber is generated by the pressure-adjusting mechanism; and
   when an object is carried into the aseptic manipulation chamber from the outside thereof, the object is stored in the first operation chamber to undergo a first decontamination that fills the first operation chamber with a decontamination gas that acts on the object and on an inner wall of the first operation chamber, the object is then moved from the first operation chamber to the second operation chamber through the communication portion to undergo a second decontamination in the second operation chamber, the second decontamination removes decontamination gas residue remaining on the object and removes decontamination gas residue remaining on the inner wall of the first operation chamber, and the object is then carried into the aseptic manipulation chamber.

2. The aseptic manipulation system according to claim 1, wherein the pressure-adjusting mechanism comprises:
   a first air supply and exhaust mechanism that supplies air to and exhausts air from the first operation chamber; and
   a second air supply and exhaust mechanism that supplies air to and exhausts air from the second operation chamber;
   the first and second air supply and exhaust mechanisms setting the air supply amount to the second operation chamber to be greater than the air supply amount to the first operation chamber, and setting the air exhaust amount from the first operation chamber to be greater than the air exhaust amount from the second operation chamber, when the communication portion is open.

3. The aseptic manipulation system according to claim 1, wherein the decontamination gas comprises a hydrogen peroxide vapor.

4. The aseptic manipulation system according to claim 1, wherein the decontamination gas residue is removed from the inner wall of the first operation chamber by aeration.

5. An aseptic manipulation system comprising an aseptic manipulation chamber, the inside of the aseptic manipulation chamber being maintained in an aseptic condition, and a decontamination chamber provided for removing microbes adhering to an object carried into the aseptic manipulation chamber from the outside;

the decontamination chamber having a first operation chamber provided with a closable inlet opening, a second operation chamber connected to the first operation chamber and provided with a closable outlet opening, and a closable communication opening for communicating between the first operation chamber and the second operation chamber, the decontamination chamber being connected to a pressure adjusting mechanism adjusting the pressure of the first operation chamber and the second operation chamber;

when the communication portion is open for communication between the first operation chamber and the second operation chamber, the inlet opening and the outlet opening are each closed, and an air current from the second operation chamber to the first operation chamber is generated by the pressure adjusting mechanism; and when an object is carried into the aseptic manipulation chamber from the outside thereof, the object is stored in the first operation chamber to undergo a first decontamination that either fills the first operation chamber with a decontamination gas that acts on the object and on an inner wall of the first operation chamber or that removes microbes adhering to the object using a first decontamination medium, the object is then moved from the first operation chamber to the second operation chamber through the communication opening to undergo a second decontamination in the second operation chamber, the second decontamination either removes decontamination gas residue remaining on the object, when the first decontamination filled the first operation chamber with the decontamination gas or that removes the microbes adhering to the object using a second decontamination medium, that is different than the first decontamination medium, when the first decontamination medium was utilized in the first decontamination, and the object is then carried into the aseptic manipulation chamber.

6. The aseptic manipulation system according to claim 5, wherein the pressure-adjusting mechanism comprises:

a first air supply and exhaust mechanism that supplies air to and exhausts air from the first operation chamber; and a second air supply and exhaust mechanism that supplies air to and exhausts air from the second operation chamber;

the first and second air supply and exhaust mechanisms setting the air supply amount to the second operation chamber to be greater than the air supply amount to the first operation chamber, and setting the air exhaust amount from the first operation chamber to be greater than the air exhaust amount from the second operation chamber, when the communication portion is open.

7. The aseptic manipulation system according to claim 5, wherein the first decontamination medium comprises a liquid decontaminant that is sprayed onto the object.

8. The aseptic manipulation system according to claim 5, wherein the first decontamination medium comprises a liquid decontaminant soaked into fabric, wherein the object is contacted by the soaked fabric.

* * * * *